United States Patent [19]

Ter-Minassian

[11] 4,072,050

[45] Feb. 7, 1978

[54] ISOTHERMAL CALORIMETRY PROCESS AND CALORIMETER FOR CARRYING OUT THE PROCESS

[75] Inventor: Leon Ter-Minassian, Fresnes, France

[73] Assignee: Agence Nationale de Valorisation de la Recherche (ANVAR), Hauts-de-Seine, France

[21] Appl. No.: 780,482

[22] Filed: Mar. 23, 1977

[30] Foreign Application Priority Data

Mar. 26, 1976 France .................................. 76 08792

[51] Int. Cl.² ........................................... G01K 17/00
[52] U.S. Cl. ............................. 73/190 R; 23/230 R; 23/253 R
[58] Field of Search ................... 73/190 R; 23/230 R, 23/253 R

[56] References Cited

PUBLICATIONS

Aven, et al., "Adiabatic Specific Heat Calorimeter for the Temperature Range 4 to 15° K," in Review of Scientific Instruments, vol. 27, No. 8, 8/56 pp. 623–628.

Primary Examiner—Herbert Goldstein
Attorney, Agent, or Firm—Diller, Brown, Ramik & Wight

[57] ABSTRACT

A calorimeter includes an adiabatic enclosure surrounding a tube for supporting a sample. In the enclosure is a control chamber in thermal contact with the sample-carrier tube and containing a substantially perfect gas. The temperature of the sample is kept constant during a change of state by varying the pressure of this gas. A differential gas thermometer provides an indication of the difference between the temperature of the sample and that of a thermally insulated reference body which is initially at the same temperature as the sample. An automatic control system varies the pressure of the gas in the control chamber in the sense which tends to cancel any temperature variations detected by the differential gas thermometer. The gas pressure is varied by means of a vertical passage which has its upper end connected to the control chamber and its lower end connected to receive hydraulic liquid from a volumetric pump actuated by the control system. The cross-section of the vertical passage decreases towards the top in such a way that the level of the liquid in the passage is in substantially linear relationship to the pressure of the gas. The quantity of thermal energy given out or taken up by the sample during the change of state is determined by measuring the variation in the pressure of the gas in the control chamber. The reference body is located coaxially around the sample-carrier tube and is coaxially surrounded by a cylindrical baffle at a thermostatically controlled temperature. The adiabatic enclosure is evacuated, and has reflective inside walls.

11 Claims, 3 Drawing Figures

ISOTHERMAL CALORIMETRY PROCESS AND CALORIMETER FOR CARRYING OUT THE PROCESS

BACKGROUND OF THE INVENTION

1. Field of the Invention

The invention concerns a calorimetry process for determining the quantity of thermal energy given out or taken up by a sample during an isothermal change of physico-chemical state, and is also concerned with a calorimeter for carrying out said process.

2. Description of the Prior Art

To measure the quantity of thermal energy given out or taken up by a sample during an isothermal change of state, the quantity of thermal energy which has to be fed to the sample or extracted from it to keep it at the same temperature during the change of state is measured. This is done by placing the sample in a calorimeter, i.e. an adiabatic enclosure. It is customary to determine the quantity of energy exchanged with the sample and the temperature of the sample by electrical means. It is difficult to obtain precise measurements of the amount of thermal energy which has to be extracted if electrical means are used, so that isothermal calorimetry is generally limited to measurements in respect of endothermic changes of state.

SUMMARY OF THE INVENTION

The object of the invention is a constant temperature calorimetry process which is equally applicable to endothermic and exothermic changes of state.

Another object of the invention is a calorimetry process in which the temperature of the sample is maintained substantially constant throughout the change of state.

The invention consists in a calorimetry process for determining the quantity of thermal energy given out or taken up by a sample during an isothermal change between two physico-chemical states, wherein said sample is maintained at a constant temperature during said change of state by varying the pressure of a gas contained in a control chamber which is in thermal contact with said sample, the quantity of thermal energy given out or taken up being determined by measuring the variation of the pressure of said gas.

If $V_q$ is the constant volume of the enclosure and P, T and $a$ are respectively the pressure, temperature and coefficient of thermal expansion of the gas, then the quantity of thermal energy taken up or given out is given by:

$$Q = V_q \int a \cdot T \, dP \qquad (1)$$

For a perfect gas $a \cdot T = 1$, so that:

$$Q = -V_q \Delta P \qquad (2)$$

The energy exchange is perfectly reversible, and depends only on the initial and final states.

Helium is one gas with properties approaching those of a perfect gas. For temperatures above 100° K and pressures of less than 50 bars, pressure variations in helium are related to the quantity of energy exchanged with an accuracy of at least 1/1000, provided that appropriate and simple corrections are made. A pressure variation of 50 bars in an enclosure volume $V_q$ of 200 cm$^3$ corresponds to an energy exchange of 1 kilojoule, which is equivalent to the melting of 3 grammes of ice, and therefore to the melting of at least 5 grammes of most organic compounds.

Operating with a constant temperature throughout the change of state has the advantage that it enables energy exchanges with the surroundings to be completely controlled.

The temperature of the sample is preferably stabilised by controlling the pressure of the gas in the control chamber by means of a closed-loop control system responsive to variations in said pressure. Variations in the temperature of the sample are preferably measured by measuring the difference between the temperatures of the sample and of a thermally insulated reference body which is initially at the same temperature as the sample, the pressure of the gas in the control chamber being varied in the sense which reduces such temperature differences to zero.

The invention also consists in a calorimeter for carrying out the above-defined process, comprising an adiabatic enclosure for receiving said sample; temperature sensing means in said enclosure responsive to the temperature of said sample; a control chamber in said enclosure, in thermal contact with said sample, and containing a gas; means external to said enclosure for varying the pressure of said gas; means external to said enclosure for indicating the pressure of said gas; and a control system adapted to actuate the pressure varying means in response to temperature variations detected by said temperature sensing means to vary the pressure of said gas in the sense required to reduce said temperature variation to zero.

The pressure variations in the control chamber are a measure of the energy exchange with the sample, which is in thermal contact with the control chamber. These pressure variations are controlled in accordance with the variation of the temperature of the sample, in order to reduce such temperature variation to zero, and so provide a measure of the energy exchange at constant temperature.

In a preferred embodiment of the invention, the calorimeter comprises a reference body is said adiabatic enclosure, and said temperature sensing means responsive to the temperature of said sample include a differential gas thermometer comprising respective first and second bulbs in thermal contact with said sample and said reference body, and a differential pressure measuring unit connected to said first and second bulbs and responsive to the difference between the pressures therein.

The use of a differential gas thermometer in conjunction with a pressure sensor provides a highly sensitive temperature sensor which has low inertia.

The reference body preferably consists of a thick-walled cylinder located coaxially around a sample-carrier tube which is in thermal contact with the control chamber and the first bulb of the differential gas thermometer, the wall of the cylinder comprising chambers which define the first bulb of the differential gas thermometer, the calorimeter further comprising a cylindrical baffle coaxially surrounding the reference body, and a thermostat system for controlling the temperature of the baffle. The sample-carrier tube and the control chamber are therefore shielded from outside influences.

The reference body and sample-carrier tube are preferably movable relative to the cylindrical baffle, between a rest position in which the baffle is in thermal contact with the reference body and a measuring position in which it is not. They are placed in the rest position to enable the temperatures to equalize, and then moved to the measuring position before any measurements are made. The adiabatic enclosure is preferably a vacuum chamber with reflective walls, and this, in combination with the movable arrangement of the reference body and sample-carrier tube, enables the temperatures to be equalized sufficiently quickly.

The means for varying the pressure of the gas in the control chamber preferably include a vertical passage with an upper portion connected to the control chamber, and a volumetric pump for supplying hydraulic fluid to the lower portion of the passage, the pump being actuated by the control system, and the passage having a cross-section which decreases towards its upper end in accordance with a law which is such that the pressure of the gas is in substantially linear relation to the height of the column of hydraulic fluid in the passage, the calorimeter further comprising means for sensing the height of the column of hydraulic fluid, connected to the control system.

Other objects and advantages of the invention will appear from the following description of an example of the invention, when considered in connection with the accompanying drawings.

DESCRIPTION OF THE PREFERRED EMBODIMENT

Figure 1:
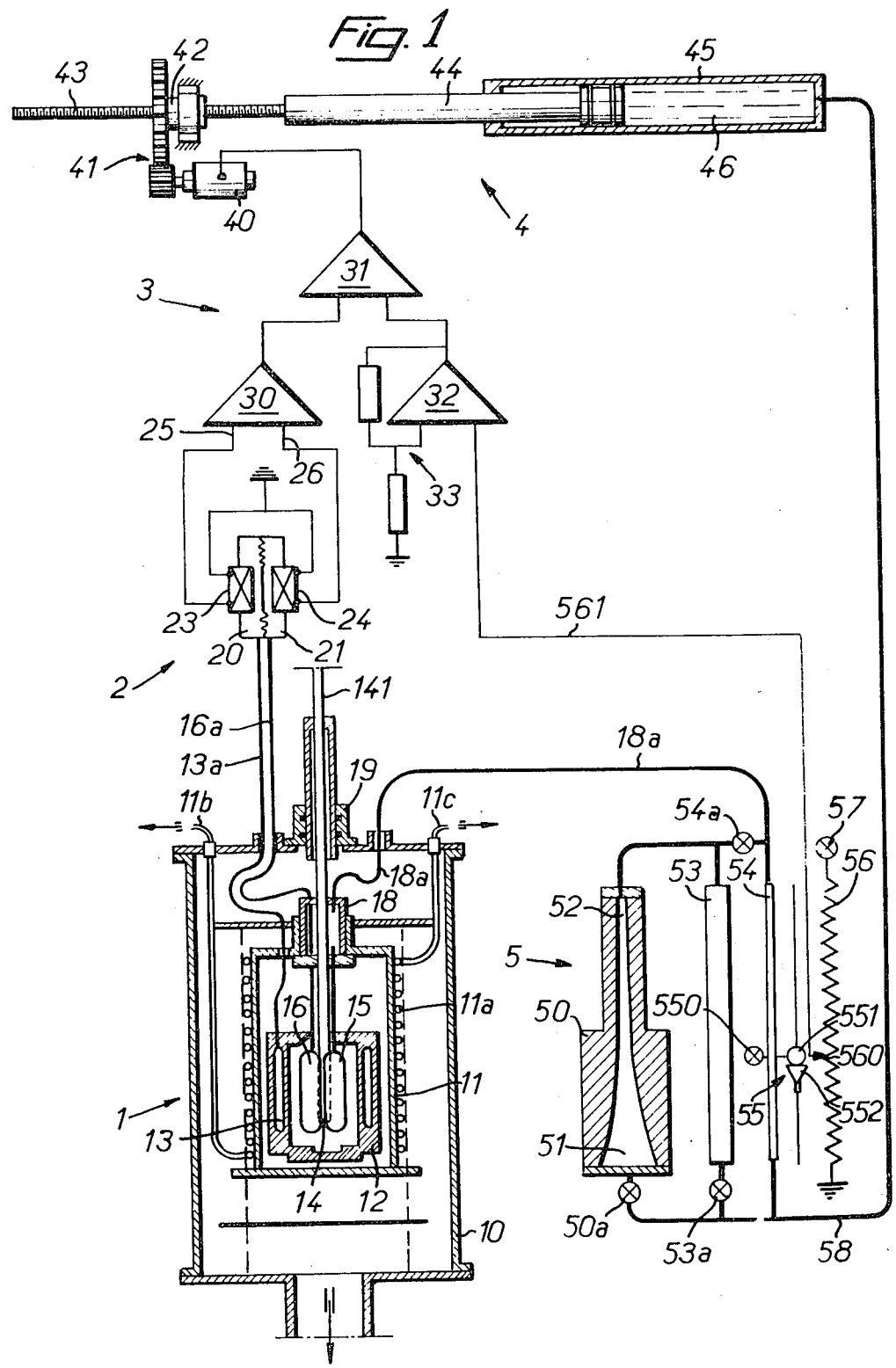
FIG. 1 is a schematic general arrangement drawing of a calorimeter in accordance with the invention.

In the selected embodiment, shown in FIG. 1, the calorimeter includes an adiabatic enclosure 1, a differential pressure measuring means 2, a control system 3, a volumetric pump 4, and a hydraulic transmission column 5.

The adiabatic enclosure 1 comprises a vacuum chamber 10 which has its inside walls polished to a highly reflective state to reduce radiation losses. Inside this is located a cylindrical baffle 11 to which is brazed a coil of tubing 11a. A fluid flows through the coil 11a, from an inlet 11b to an outlet 11c, the temperature of this fluid being controlled by means of a thermostat (not shown) external to the adiabatic enclosure, so that the temperature of the baffle 11 can be accurately controlled. The baffle 11 is centred in the enclosure 10 by means of a conventional system of support feet and baffles, providing good mechanical stability with minimal exchange of heat between the baffle 11 and the enclosure 10.

Figure 2:
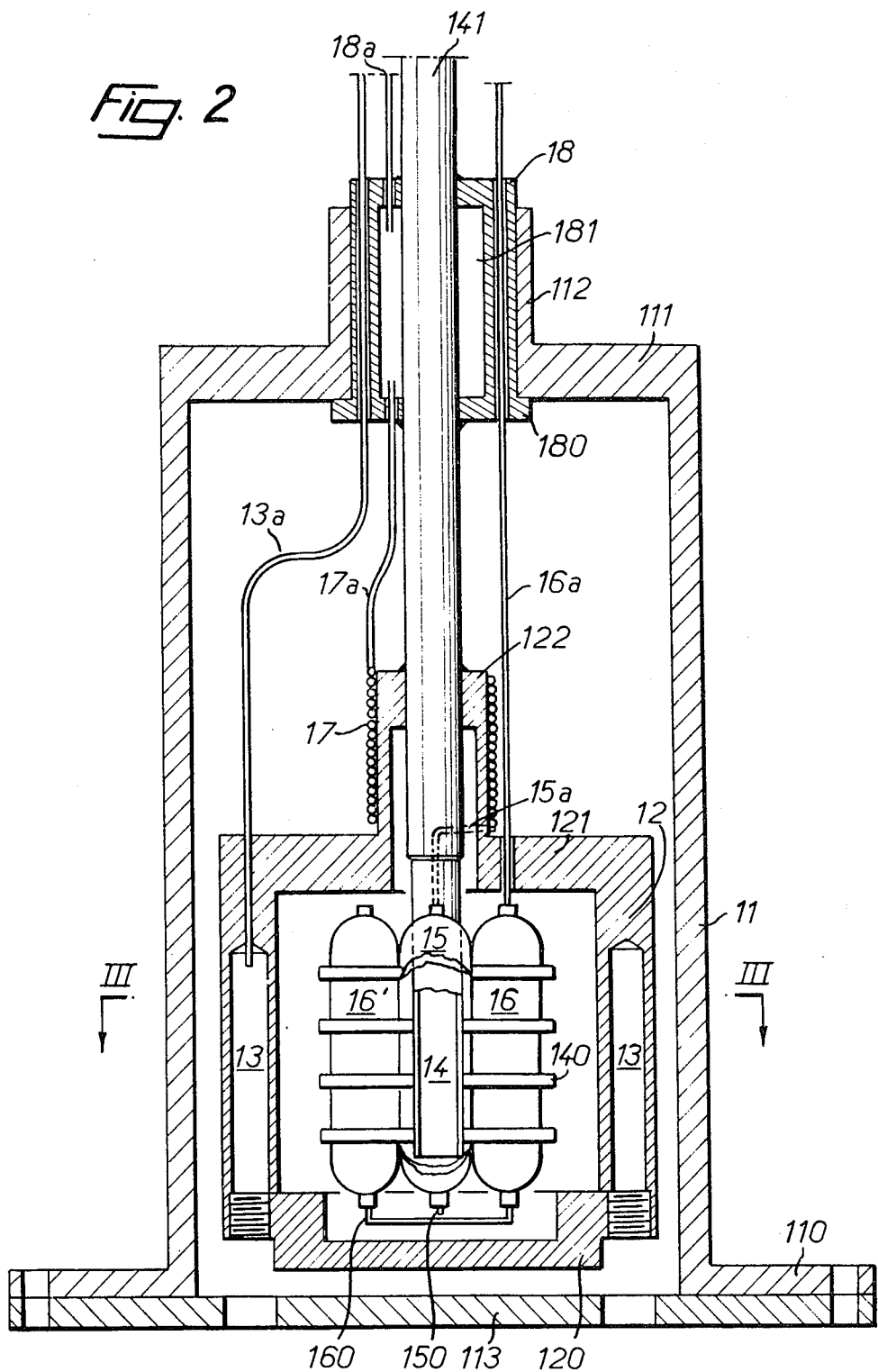
FIG. 2 is a cross-section through the adiabatic enclosure of the calorimeter.
Figure 3:
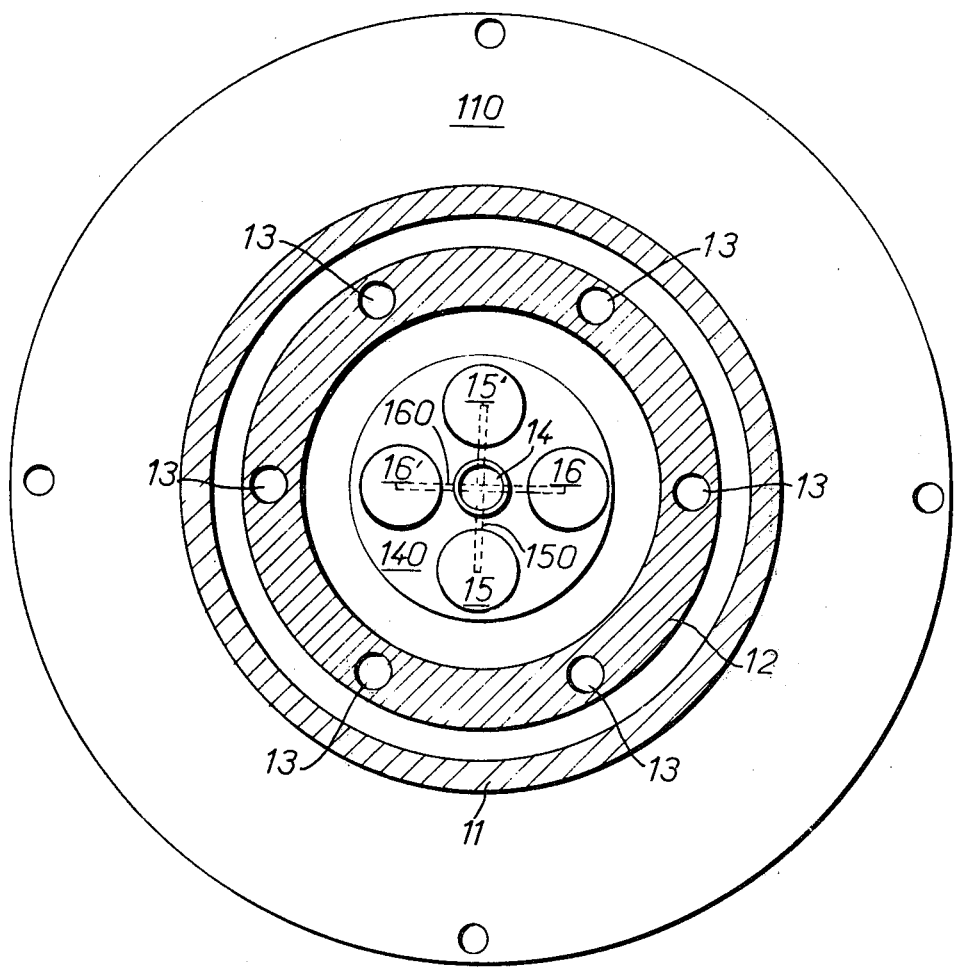
FIG. 3 is a cross-section on the line III—III in FIG. 2.

As can be seen more clearly in FIGS. 2 and 3, in which the coil of tubing 11a is not shown, the cylindrical baffle 11 has a flange 110 at its lower end, to which is attached a closure plate 113. The upper end of the baffle 11 is closed by a top plate 111, in the centre of which is a cylindrical neck 112. A bush 18 can slide freely in the neck 112, and has a flange 180 at its lower end. Through the hollow space 181 in the bush 18 passes a tube 141 which is an extension of the sample-carrier tube 14, which is aligned with the axis of the cylindrical baffle 11.

A reference body 12 is located around the sample-carrier tube 14, and consists of a thick-walled cylinder coaxial with the baffle 11. Chambers 13 are bored out of the thick wall of the cylinder 12, and communicate with one another through narrow passages (not shown). The chambers 13 are connected to a capillary tube 13a which passes longitudinally through the cylindrical wall of the bush 18, and so to the outside of the baffle 11. The reference body 12 is closed at its lower end by a plate 120 which has a flat surface facing and parallel to the closure plate 113. The upper end of the reference body 12 is closed by a top plate 121 with a cylindrical neck 122 at its centre, the upper end of the neck 122 being brazed to the tube 141. When the tube 141 is lowered, the bush 18 slides in the neck 112, and the flat surface of the bottom plate 120 of the reference body 12 rests on the closure plate 113.

Around the sample-carrier tube 14 are located four tubular capsules 15, 15', 16 and 16', crimped into rings 140 attached to the tube 14. Capsules 15 and 15' are diametrically opposite one another and are connected together by a capillary tube 150. Similarly, capsules 16 and 16' form a diametrically opposed pair connected together by a capillary tube 160. Capsule 16 is connected to a capillary tube 16a which passes longitudinally through the cylindrical wall of the bush 18. A capillary tube 15a connected to capsule 15 has a section 17 tightly wound round the cylindrical neck 122 of the reference body 12, and a section 17a which leads to the hollow space 181 inside the bush 18. A capillary tube 18a extends upwardly out of the space 181. The capsule pairs 15/15' and 16/16' have the same internal volume, which is equal to the total volume of the set of six chambers 13 in the reference body 12.

Referring again to FIG. 1, the chambers 13 and the capsules 16/16' are connected by respective capillary tubes 13a and 16a to respective chambers 20 and 21 of a differential pressure transducer 2. A flexible membrane 22 separates the two chambers 20 and 21, and its position is sensed by two sensors 23 and 24. The signal which appears between the outputs 25 and 26 of the sensors 23 and 24, respectively, is representative of the difference between the pressures in chambers 20 and 21.

The chambers 13, 20 and 21, the capillary tubes 13a and 16a, and the capsules 16 and 16' are filled with a substantially perfect gas, such as helium. The assembly forms a very sensitive differential gas thermometer, with a resolution of $4.10^{-6}$ ° K at a temperature of 300° K.

The capillary tube 18a connects the capsules 15 and 15' to the upper end of the hydraulic transmission column 5, which comprises three vertical components, a main column 50 with a cross-section which decreases towards its upper end, an auxiliary column 53, and a transparent level-indicator tube 54. The three components 50, 53 and 54 have their lower ends connected to a line 58 which receives hydraulic liquid from the volumetric pump 4. The columns 50 and 53 can be isolated from the line 58 by means of taps 50a and 53a, respectively. The upper ends of the columns 50 and 53 can be isolated from the level-indicator tube 54 and from the capillary tube 18a by means of a tap 54a.

The capsules 15 and 15' and the upper end of the column 50 are filled with helium, which is pressurised by pumping hydraulic liquid into the lower end of the column 50 through the line 58. The cross-section of the column 50 decreases in accordance with a law such that, when the taps 50a and 54a are both open, the changes in the level of the hydraulic liquid in the main column 50 and in the level-indicator tube 54 are linearly related to the variations in the pressure of the helium.

This law can easily be calculated by an experienced technician, from the basis of Mariotte's law.

A known form of level-follower device 55 is located along the length of the level-indicator tube 54, and comprises a light source 550, a photosensitive assembly 551, and a servo-system 552. A change in the light level at the photosensitive assembly 551 due to movement of the hydraulic liquid meniscus causes the servo-system 552 to move the level-follower device 55 in the appropriate sense. The follower 55 is connected to the cursor 560 of a potentiometer 56 connected across a voltage source 57. The cursor 560 is connected to an electrical lead 561, and the voltage on this lead 561 is an accurate measure of the level of the hydraulic liquid in the tube 54 and in the main column 50. This voltage is therefore proportional to the pressure in the capsules 15 and 15'.

The volumetric pump 4 consists of a known form of electrically driven ram, and comprises a reversible electric motor 40 which, through gearing 41, drives a nut 42 located on a lead-screw 43. The lead-screw 43 is coupled to the piston rod 44 of a hydraulic ram 45 containing hydraulic liquid 46 which can be pumped into the line 58 by advancing the piston rod 44.

The control system includes a differential amplifier 30 with its inputs connected to the outputs of the differential pressure transducer 2. Its output is connected to one input of a power amplifier 31 which drives the motor 40 of the volumetric pump 4. The gain of the power amplifier 31 is controlled by a signal received on a second input from a differential amplifier 32 which has one input connected to the electrical lead 561, to receive the output voltage of the potentiometer 56. The other input is connected to a frequency-selective feedback network 33 which matches the output voltage of the amplifier 32 to the rate at which the voltage from potentiometer 56 varies.

OPERATION

A sample is placed in the sample-carrier tube 14, through the extension tube 141, which is then lowered until the base plate 120 of the reference body 12 rests on the closure plate 113 of the baffle 11 (FIG. 2). The operating temperature is then set by passing a liquid at the appropriate temperature through the coil of tubing 11a. While the temperatures equalize and stabilize, the capillary tubes 13a and 16a are connected together by means of a tap (not shown), to avoid overloading the differential pressure transducer 2.

During this period, while the calorimeter acquires the required temperature, the initial pressure in the capsules 15 and 15' is set by operating the ram 4 manually, and the initial level of the hydraulic liquid in the main column 50 is set by manipulating the taps 50a, 53a and 54a.

When the temperatures of the reference body 12 and the sample-carrier tube 14 are the same, which is verified by cutting off the communication between capillary tubes 13a and 16a, the extension tube 141 is raised. The vacuum in the enclosure 10 is maintained by the sliding seal 19. The reference body 12 is then thermally isolated from the baffle 11, the temperature of which is thermostatically controlled. The control system 3 is then brought into operation.

At this point, the change of physico-chemical state for which the latent energy is to be determined is started. The resulting variations in the temperature of the sample-carrier tube 14 and capsules 16 and 16' cause a differential pressure variation which is sensed by the transducer 2. This causes the control system 3 to drive the volumetric pump 4, which varies the pressure in the transmission column 5 and in the capsules 15 and 15', which form a control chamber. The variation in the pressure in this control chamber results in an exchange of energy with the sample-carrier assembly which balances out the amount of energy given out or taken up by the sample. The gas which is admitted to the capsules 15 and 15' is at the same temperature as the reference body 12, as a result of its passage through the space 181 in the bush 18, which is in thermal contact with the baffle 11, and through the coiled section 17 of the capillary tube, which is in thermal contact with the reference body 12.

Although the differences between the temperatures of the sample-carrier tube 14 and the reference body 12, which result in differential pressure variations at the transducer 2, are substantially proportional to the variations of the internal energy of the system comprising the sample, the sample-carrier tube and the control chamber, movement of the piston rod of the ram 4 causes pressure variations in the transmission column 5 and in the capsules 15 and 15' which are inversely proportional to the displacement of the piston rod. For this reason, the gain of the power amplifier 31 is controlled by the output signal from the amplifier 32, which is varied in accordance with the level of hydraulic liquid in the transmission column 5 by the level-follower device 55 coupled to the cursor of the potentiometer 56. The overall gain of the control loop can thus be linearised, the loop comprising the differential gas thermometer (chambers 13, bulbs 16 and 16', and pressure transducer 2), the control amplifier circuitry 3, the volumetric pump 4, the transmission column 5, and the control chamber (bulbs 15 and 15').

Spurious exchanges of energy between the sample-carrier tube and the surroundings are minimised by the coaxial arrangement of the sample-carrier tube 14, the reference body 12, the baffle 11, and the vacuum chamber 10. Differences between the temperatures of the sample-carrier tube 14 and the reference body 12 are limited, during the period in which measurements are carried out, to very small values, so that heat exchange between the tube 14 and the body 12 can be neglected.

It will be understood that various changes in the details, materials and arrangement of parts which have been described herein for the purpose of explaining the nature of the invention may be made by those skilled in the art, without departing from the scope of the invention as expressed in the following claims.

I claim:

1. A calorimetry process for determining the quantity of thermal energy given out or taken up by a sample during an isothermal change of state between two physico-chemical states, wherein said sample is maintained at a constant temperature during said change of state by varying the pressure of a gas contained in a control chamber which is in thermal contact with said sample, the quantity of thermal energy given out or taken up being determined by measuring the variation of the pressure of said gas.

2. A process as set forth in claim 1, wherein the temperature of said sample is stabilized by controlling the pressure of said gas by means of a closed-loop control system responsive to variations in said pressure.

3. A process as set forth in claim 1, wherein the difference between the temperatures of said sample and a thermally insulated reference body which is initially at the same temperature as said sample is measured, the pressure of said gas being varied in the sense which tends to reduce said temperature difference to zero.

4. A calorimeter, comprising an adiabatic enclosure for receiving a sample, temperature sensing means in said enclosure responsive to the temperature of said sample, a control chamber in said enclosure, in thermal contact with said sample and containing a gas, means external to said enclosure for varying the pressure of said gas, means external to said enclosure for sensing the pressure of said gas, and a control system adapted to actuate said pressure varying means in response to temperature variations detected by said temperature sensing means, to vary the pressure of said gas in the sense required to reduce said temperature variations to zero, the quantity of thermal energy given out or taken up by said sample during an isothermal change between two physico-chemical states being determined by measuring the variation of the pressure of said gas.

5. A calorimeter as set forth in claim 4, further comprising a reference body in said enclosure, and wherein said temperature sensing means responsive to the temperature of said sample include a differential gas thermometer comprising respective first and second bulbs in contact with said sample and said reference body, and a differential pressure sensing unit connected to said bulbs and responsive to the difference between the pressures in said first and second bulbs.

6. A calorimeter as set forth in claim 5, further comprising a sample-carrier tube which is in thermal contact with said control chamber and with said first bulb of said differential gas thermometer, and wherein said reference body consists of a thick-walled cylinder located coaxially around said sample-carrier tube, the wall of said cylinder including chambers which define said first bulb, said calorimeter further comprising a cylindrical baffle coaxially surrounding said reference body, and a thermostat system for controlling the temperature of said baffle.

7. A calorimeter as set forth in claim 6, further comprising means for moving said reference body and said sample-carrier tube relative to said cylindrical baffle, between a rest position in which said baffle is in thermal contact with said reference body, and a measuring position in which said baffle is not in thermal contact with said reference body.

8. A calorimeter as set forth in claim 6, wherein said system for varying the pressure of said gas is connected to said control chamber by a conduit which includes a first section in thermal contact with said tubular baffle and a second section in thermal contact with said reference body.

9. A calorimeter as set forth in claim 4, wherein said adiabatic enclosure comprises a vacuum chamber with reflective walls.

10. A calorimeter as set forth in claim 4, wherein said means for varying the pressure of said gas include means defining a vertical passage, an upper portion of said passage being connected to said control chamber, and a volumetric pump for supplying hydraulic liquid to the lower portion of said passage, said pump being actuated by said control system.

11. A calorimeter as set forth in claim 10, wherein said volumetric pump includes a cylinder, a piston in said cylinder, and an electric motor coupled to said piston to move it linearly in said cylinder, said vertical passage having a horizontal cross-section which decreases towards its upper end in accordance with a law which is such that the pressure of said gas is substantially linearly related to the height of the column of hydraulic liquid in said passage, the calorimeter further comprising means for sensing the height of said column of hydraulic liquid, said height sensing means being connected to said control system.

* * * * *